US012669430B2

(12) United States Patent
Uehlinger et al.

(10) Patent No.: US 12,669,430 B2
(45) Date of Patent: Jun. 30, 2026

(54) PHOTOACOUSTIC GAS SENSOR DEVICE

(71) Applicant: SENSIRION AG, Stäfa (CH)

(72) Inventors: Thomas Uehlinger, Stäfa (CH);
Christophe Salzmann, Stäfa (CH)

(73) Assignee: Sensirion AG, Stäfa (CH)

( * ) Notice: Subject to any disclaimer, the term of this
patent is extended or adjusted under 35
U.S.C. 154(b) by 213 days.

(21) Appl. No.: 18/279,062

(22) PCT Filed: Feb. 24, 2022

(86) PCT No.: PCT/EP2022/054716
§ 371 (c)(1),
(2) Date: Aug. 27, 2023

(87) PCT Pub. No.: WO2022/184553
PCT Pub. Date: Sep. 9, 2022

(65) Prior Publication Data
US 2024/0133801 A1     Apr. 25, 2024
US 2024/0230519 A9     Jul. 11, 2024

(30) Foreign Application Priority Data

Mar. 5, 2021     (EP) ..................................... 21161060

(51) Int. Cl.
*G01N 21/17*          (2006.01)
*G01N 29/24*          (2006.01)
(Continued)

(52) U.S. Cl.
CPC ..... *G01N 21/1702* (2013.01); *G01N 29/2425*
(2013.01); *G01N 29/44* (2013.01);
(Continued)

(58) Field of Classification Search
None
See application file for complete search history.

(56) References Cited

U.S. PATENT DOCUMENTS 10,302,554 B2     5/2019   Tumpold et al.
10,753,858 B2 *   8/2020   Kolb .................. G01N 21/1702
(Continued)

FOREIGN PATENT DOCUMENTS

EP          3614126 A1       2/2020
JP       2011252906 A       12/2011
(Continued)

OTHER PUBLICATIONS

International Search Report and Written Opinion for corresponding
Application No. PCT/EP2022/054716, issued May 19, 2022.

*Primary Examiner* — Suman K Nath
(74) *Attorney, Agent, or Firm* — Renner, Otto, Boisselle
& Sklar, LLP

(57)          ABSTRACT
A photoacoustic gas sensor device for determining a value
indicative of a presence or a concentration of a chemical
component in a gas comprises a substrate and a measure-
ment cell body arranged on a first side of the substrate. The
substrate and the measurement cell body define a measure-
ment cell. A cap is arranged on the first side of the substrate
within the measurement cell. The cap and the substrate
define a cap volume. The cap and the substrate acoustically
seal the cap volume. A measurement volume is confined by
the measurement cell body, the substrate and the cap. An
aperture is provided in the measurement cell for the gas to
enter the measurement volume. Electrical components are
arranged on the first side of the substrate and in the mea-
surement cell.

19 Claims, 4 Drawing Sheets

(51) Int. Cl.
    *G01N 29/44*         (2006.01)
    *G01N 33/00*         (2006.01)

(52) U.S. Cl.
    CPC ... *G01N 2021/1704* (2013.01); *G01N 33/004*
        (2013.01); *G01N 2201/0221* (2013.01); *G01N*
           *2291/021* (2013.01); *G01N 2291/02809*
             (2013.01); *G01N 2291/101* (2013.01)

(56) References Cited

U.S. PATENT DOCUMENTS

| | | |
|---|---|---|
| 2016/0313288 A1 | 10/2016 | Theuss et al. |
| 2021/0181158 A1* | 6/2021 | Schaller ............... G01N 29/348 |
| 2022/0236230 A1* | 7/2022 | Salzmann .......... G01N 21/1702 |

FOREIGN PATENT DOCUMENTS

| | | |
|---|---|---|
| JP | 2021025923 A | 2/2021 |
| WO | 2018097071 A1 | 5/2018 |
| WO | 2021028231 A1 | 2/2021 |

* cited by examiner

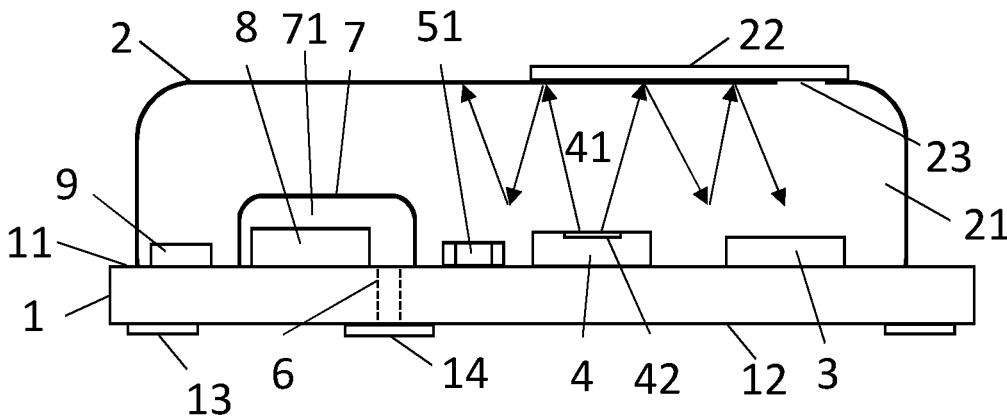
Fig. 3
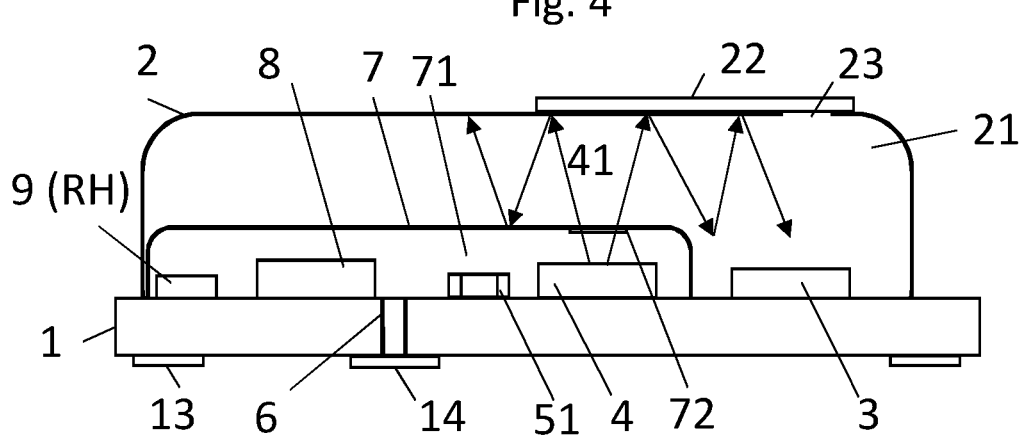
Fig. 4
Fig. 5

PHOTOACOUSTIC GAS SENSOR DEVICE

This application is a national phase of International Application No. PCT/EP2022/054716 filed Feb. 24, 2022, which claims priority to European Patent Application No. 21161060.5 filed Mar. 5, 2021, each of which is hereby incorporated herein by reference in its entirety.

TECHNICAL FIELD

The present invention relates to a photoacoustic gas sensor device which is configured to determine a value indicative of a presence or a concentration of a component, in particular of $CO_2$, in a gas.

BACKGROUND ART

Photoacoustic gas sensors rely on the physical effect that e.g. infrared radiation is absorbed by molecules of a component of interest in a gas, e.g. $CO_2$, thereby transferring the molecules to an excited state. Subsequently heat is generated due to non-radiative decay of the excited state, e.g. by collisions of the molecules, which leads to an increase of pressure. Through modulating the infrared radiation to be absorbed with a modulation frequency, the pressure varies at the modulation frequency. Such pressure variation may be measured by a pressure transducer. The concentration of the component is proportional to an amplitude of the pressure variation.

The radiation emitter, the pressure transducer and a controller for controlling the radiation emitted can be arranged in the same volume, in which the photoacoustic reaction takes place, i.e. a measurement volume of a photoacoustic measurement cell. This is beneficial in terms of a small footprint of the gas sensor device. However, e.g. the controller, when switching currents for modulating the emission of the radiation from the radiation source, heats up and cools down at the same frequency the electromagnetic radiation source emits the modulated radiation. Such pulsed heating in turn amplifies the pressure variations in the measurement cell and hence falsifies the signal supplied by the pressure transducer by adding an offset.

It is hence an object of the present invention to provide a photoacoustic gas sensor device, the measurement signal of which is less prone to sound and/or temperature variations induced by the controller and/or other electrical components of the gas sensor device.

DISCLOSURE OF THE INVENTION

The object is achieved by a photoacoustic gas sensor device according to claim 1.

The photoacoustic gas sensor device—also abbreviated as PA gas sensor device—allows for determining a value indicative of a presence or a concentration of a chemical component in a gas. The PA gas sensor device comprises a substrate and a measurement cell body arranged on a first side of the substrate. This includes a mounting of the measurement cell body direct on the substrate, as well as a mounting of the measurement cell body on any intermediate component between the substrate and the measurement cell body, as may be, as long as the measurement cell body is arranged at the first side of the substrate, but not its opposite side. The substrate and/or any intermediate component, as well as and the measurement cell body define a measurement cell. A cap is arranged on the first side of the substrate within the measurement cell. The cap and the substrate define a cap volume. In one embodiment, the cap itself significantly or even completely contributes to the cap volume in case the cap defines an interior space, e.g. by means of vertical walls, or by means of a concave shaped interior, or by means of any other cavity in the cap. In a different embodiment, the substrate significantly or even completely contributes to the cap volume by means of a recess therein, which recess is covered by a planar cap. In a further embodiment, both, the cap and the substrate contribute to the cap volume by means of a recess in der substrate partially contributing to the cap volume and by means of a cavity in the cap partially contributing to the cap volume.

The measurement cell, the substrate and the cap, e.g. parts or all of its outer surface, in turn define a measurement volume in which the photoacoustic conversion takes place. The measurement cell comprises an aperture for the gas to enter the measurement volume.

The cap volume is acoustically sealed, such that the photoacoustic conversion in the measurement volume is not affected by electrical components resident in the cap volume. I.e., pressure variations in the acoustic spectrum in the cap volume are banned or at least reduced from propagating into the measurement volume. The acoustic seal property may include that the cap, the substrate, and any potential mechanical interface in between are designed and/or configured as to not let pass pressure variations from the cap volume into the measurement volume.

Electrical components are arranged on the first side of the substrate and in the measurement cell. This does not exclude that additional electronic components may be arranged on the substrate outside the measurement cell, in case the substrate extends beyond its area covered by the measurement cell body. Preferably, the electrical components are interconnected by conductor tracks on or in the substrate. The electrical components arranged in the measurement cell comprise at least an electromagnetic radiation source—also abbreviated as EM radiation source—for emitting electromagnetic radiation into the measurement volume, a pressure transducer for measuring a sound wave generated by the chemical component in response to an absorption of the electromagnetic radiation by the chemical component present in the measurement volume, and a controller configured to control the electromagnetic radiation source. The pressure transducer is arranged outside the cap volume while at least one of the electrical components other than the pressure transducer is arranged in the cap volume.

The PA gas sensor device relies on the photoacoustic effect: Molecules of a chemical component of interest, e.g. $CO_2$ in the ambient gas, e.g. the ambient air, absorb electromagnetic radiation, which in a preferred example is radiation in the infrared band, leading to a generation of heat due to non-radiative decay, e.g. by collisions between the molecules of the chemical component of and/or by collisions of the molecules of the chemical component with different molecules, which in turn leads to an increase of pressure. By modulating an intensity of the EM radiation with a modulation frequency, including an ON/OFF modulation of the EM radiation source, a modulation of pressure may be achieved. Such pressure modulation or pressure variations, i.e. sound waves, may be measured by the pressure transducer, e.g. a microphone. The value indicative of a presence or a concentration of the chemical component, i.e. the chemical component's concentration, may then be determined dependent on the pressure variations, in particular dependent on an amplitude of the pressure variations, since the amplitude may be assumed to be proportional to an amount of EM radiation absorbed by the chemical component, and hence proportional to the chemical component's concentration in the gas if all other factors, e.g. a mean optical path length in the measurement volume, stay equal.

In addition to the EM radiation source and the pressure transducer, the PA gas sensor device comprises further electrical components, including a controller configured to control the EM radiation source. The controller is arranged on the same side of the substrate as the other electrical components, i.e. on its first side and in the measurement cell. The controller is configured to control an intensity of the electromagnetic radiation to modulate with the modulation frequency. The modulation frequency is between 1 Hz and 100 kHz, preferably between 10 Hz and 200 Hz, more preferably between 20 Hz and 60 Hz, e.g. 40 Hz. Preferably, a heater of the EM radiation source is switched with the modulation frequency.

In a very preferred embodiment, in addition to controlling the EM radiation source, the controller is configured to process an electrical signal supplied by the pressure transducer and to determine the value indicative of a presence or a concentration of the chemical component dependent on this electrical signal. In this respect, the controller preferably performs signal processing such as filtering and/or linearization and/or compensation and/or A/D conversion. In particular the value is determined dependent on an amplitude of the electrical signal, e.g. a loudness in the case of a sound wave. Preferably the measurement signal is bandpass-filtered around the modulation frequency. This increases a robustness of the determination since sound waves with other frequencies are not taken into account.

At least one electrical component other than the pressure transducer is arranged in the cap volume. Preferably, the one or more electrical components arranged in the cap volume may impact the photoacoustic conversion when arranged in the measurement volume instead of the cap volume. Such electrical component may include a component responsible for pressure variations and/or heat variations in its surroundings; and/or a component with non-reflective surfaces detrimentally impacting reflectivity of the electromagnetic radiation emitted by the EM radiation source; and/or a component requiring enhanced mechanical protection to be provided by the cap; and/or a component requiring a dedicated access to the ambient of the photoacoustic gas sensor granted.

Given that modulating the EM radiation source is achieved by modulated or switched currents in the controller, the controller heats up and cools down at the same frequency the EM radiation source emits the pulsed radiation. This impacts the atmosphere in the measurement cell and evokes pressure variations with the same frequency with the pressure variations evoked by the chemical component interacting with the modulated EM radiation in case the controller were arranged in the measurement volume.

For avoiding adding such controller induced offset to the pressure signal—which effect of adding offset is also referred to as crosstalk scenario—, the controller preferably is separated from the measurement volume by means of the cap. Accordingly, by introducing the cap, a measurement volume of the present PA gas sensor device now is defined by the measurement cell body, the substrate and the cap, and in particular is separated from the cap volume that may be reserved for electrical components with an adverse impact on the photoacoustic conversion.

In a very preferred embodiment, the controller is embodied as integrated circuit, and specifically as ASIC (Application Specific Integrated Circuit). This helps to miniaturize the PA gas sensor device. However, the integrated circuit representing the controller can even be embodied as bare die of chip scale package which may even more reduce the footprint of the PA gas sensor device. On the other hand, such embodiment of a controller may require additional mechanical protection which then is supplied by the cap.

An electrical component preferably arranged in the cap volume may include a transistor, in particular a power transistor, and/or a component including such transistor. Such component may be a voltage controller. Accordingly, it is preferred that one or more transistors, and/or components with one or more transistors, is/are arranged in the cap volume.

The same may also be true for passive electric components, such as a capacitor, a resistance, or a coil, which under the application of switched currents may impact the surroundings with pressure variations. Accordingly, it is preferred to arrange such one or more passive components in the cap volume.

An electrical component arranged under the cap in the cap volume may include a bulky component with a top surface exceeding $9$ mm$^2$, or, more preferably with a top surface exceeding $3$ mm$^2$. The top surface may be defined as surface of the component except the portion facing the substrate. In case such top surface may be not be reflective or may not be coated to reflect EM radiation the measurement volume, reflectivity in the measurement volume is decreased. This may be a reason to position such electrical component in the cap volume.

The cap is mounted onto the first side of the substrate, and preferably establishes an acoustic barrier and/or acoustic seal of the cap volume against the measurement volume, and/or a thermal barrier and/or thermal seal. Accordingly, the cap causes, that no or only negligible pressure variations propagate from the cap volume into the measurement volume. Accordingly, it is preferred that the cap including and its mounting onto the substrate limit or avoid a gas exchange between the cap volume and the measurement volume, and hence, a transfer of medium.

Also thermal variations caused from the operation of an electric component may have an adverse effect. However, the cap limits or avoids a transition of thermal variations from the cap volume into measurement volume at the same time, given that heat emitted from the electrical component/s under the cap is isolated in and by the cap volume and the medium therein. In case the cap volume is evacuated, a thermal impact on the measurement volume originating from the cap volume may even be less.

The cap preferably is made from a material preventing such gas exchange there through. This also includes that the cap is free from holes or other openings allowing a gas exchange between the cap volume and the measurement volume. This also includes that the cap is mounted onto the substrate in a sealing manner, preferably by means of an adhesive or a solder. E.g. the cap is made from a gas-tight material.

Accordingly, crosstalk, in particular thermal and/or acoustic crosstalk can be prevented from the controller into the measurement volume and finally onto the pressure transducer. No or negligible controller induced offset is added to the pressure signal supplied by the pressure transducer.

The cap may comprise or may be made from an electrically conducting material. Such choice of material may provide for an additional effect in that the electrical component in the cap volume, such as the controller, may be EM shielded by the cap. Given that the controller preferably is embodied as an integrated circuit that is sensitive to the impact of electromagnetic radiation, and on the other hand the EM radiation source emits EM radiation that is also potentially detrimental to the integrated circuit, the cap may also protect the controller in this scenario, in particular in case the EM radiation source is arranged outside the cap on the substrate, i.e. outside the cap volume.

The PA effect in the measurement cell relies onto a good reflectivity of all the surfaces defining the measurement volume for the EM radiation emitted. While the inner surface of the measurement cell body and the first side of the substrate are such surfaces, the (outer) surface of the cap, i.e. the surface of the cap facing and defining the measurement volume is also critical for the overall reflectivity in the PA gas sensor device. Accordingly, it is preferred, that such surface of the cap facing the measurement volume has a reflectivity of more than 70%, preferably more than 80%, more preferably more than 90%. In combination with the inner surface of the measurement cell body showing a reflectivity of more than 70%, preferably more than 80%, more preferably more than 90%, and potentially with reflective coatings on the substrate surfaces and/or electrical components facing the measurement cell, the overall reflectivity of surfaces defining the measurement volume can be improved.

In particular, the cap is made from metal. In a different embodiment, the cap is made from plastics coated with metal on its outside surface facing the measurement volume. In this embodiment, reflectivity and electromagnetic shielding can be achieved at the same time. The same choices of material are preferred for the measurement cell body. In case of the measurement cell body is made from plastics, its inner surface may be coated with metal resulting in a reflective coating. Such coatings may by be made e.g. from one of gold, aluminum, nickel, copper. Gold is also particularly convenient for plating the substrate, e.g. the PCB, since it is anyways applied as a corrosion protection to a surface of conductors during forming of the PCB. In another embodiment, the measurement cell body is made from sheet metal, e.g. by deep drawing. Sheet metal has the advantages of being mechanically stable even at low thickness, and of showing a high reflectivity for electromagnetic radiation even without any further coating. Preferably the measurement cell body and the substrate are connected in a gas-tight manner, e.g. by gluing or soldering. Advantageously the measurement cell is acoustically tight.

All these measures contribute to a longer mean optical path length of the EM radiation within the measurement volume. In this way, the mean optical path length within the measurement volume may be increased to >1 cm, preferably >3 cm, more preferably >5 cm. This in turn facilitates the measurement cell to be small, e.g. dimensions of the measurement cell are smaller than 2×2×2 cm³, preferably smaller than 1×1×1 cm³. The entire photoacoustic gas sensor device may have a size of e.g. 1×1×0.7 cm³ in particular smaller than conventional photoacoustic gas sensors having a linear optical path length.

The present PA gas sensor device hence offers a small footprint, however, not at the cost of signal performance.

Preferably, the substrate comprises a venting hole arranged to connect the cap volume to an ambient of the photoacoustic gas sensor device. Accordingly, in the area of the substrate that is covered by the cap, a through channel is provided from the first side of the substrate to its second side—i.e. from its front side to its back side—to allow an exchange of gas between the cap volume and the ambient. Such venting hole may be preferred in order to allow a pressure equilibrium be achieved, e.g. after a heating of the cap volume, e.g. during manufacturing or assembly processes. A diameter of such venting hole preferably is between 100 µm and 300 µm. In order to protect the cap volume from particles or liquids, a venting hole membrane may be provided which covers the venting hole, which is impermeable to liquids but permeable to gas. Preferably, the venting hole membrane is attached to the substrate, e.g. at its first side, or at its second side, i.e. the back side facing the ambient. This arrangement is beneficial in terms of manufacturing. After manufacture of the measurement cell, the venting hole membrane can be attached to the substrate in a final step. In a different embodiment, the venting hole membrane is attached during the preparation of the substrate, before the measurement cell body is attached to the substrate.

In a preferred embodiment, the electrical components include another sensor for sensing an environmental parameter. This sensor is referred to as "other sensor" given that the pressure transducer represents a sensor, too. The other sensor may be configured to sense one or more of humidity and/or pressure and/or chemical components in the gas. Accordingly, the other sensor may be embodied as one or more of a pressure sensor, a barometric pressure sensor, another pressure transducer, another gas sensor, e.g. of metal oxide type or of electrochemical type.

In one embodiment, the electrical signal provided by the other sensor is supplied at an output of the PA gas sensor device, e.g. for providing additional information on the measurement scenario. In a different embodiment, the signal of the other sensor is used to improve the signal supplied by the pressure transducer, e.g. by compensating for effects of the measured environmental variable onto the gas concentration in the measurement volume. Hence effects of ambient conditions on the measurement can be reduced or eliminated. Such compensation makes a resulting concentration value more accurate and more reliable, or in other words, the gas sensor device may be applied in varying environmental conditions.

For both purposes, the other sensor can be either arranged inside the cap volume or outside the cap volume in the measurement cell. When arranged inside the cap volume, and in case of a venting hole in the substrate, ambient gas may enter the cap volume and the desired variable of the ambient may be sensed by the other sensor. In such scenario, the venting hole membrane may show different characteristics e.g. in terms of diffusion, selectivity, etc. that the membrane covering the aperture in the measurement cell body to be introduced in more detail later on. When arranged outside the cap volume, ambient gas may enter the measurement volume by the aperture and the desired variable of the ambient may be sensed therein.

In one embodiment of the present invention, the EM radiation source is arranged in the cap volume. In this embodiment, the cap includes an optical window arranged and configured to enable the radiation emitted by the EM radiation source to enter the measurement volume and/or bandpass filter the radiation emitted by the EM radiation source before entering the measurement volume.

In a different embodiment, when the EM radiation source is arranged outside the cap volume and is configured to emit ultraviolet radiation, it is preferred that the cap is made from a material opaque to ultraviolet radiation to protect the controller in the cap volume therefrom.

While EM radiation applied generally can be any radiation in the spectrum from radio to ultraviolet, the EM radiation preferably used is infrared radiation. This means that the EM radiation source is an infrared radiation source for emitting infrared radiation. Infrared radiation preferably is defined as radiation having a wavelength in a range between 700 nm and 1 mm. In this embodiment, the pressure transducer is configured to measure the sound wave generated by the component in response to the absorption of the infrared radiation by the component. In another embodiment, the electromagnetic radiation source is a source for emitting radiation of a wavelength in a range between 100 nm and 700 nm.

Preferably, the EM radiation emitted by the EM source is only emitted in a band matching an absorption peak of the chemical component of interest. A band is considered a subrange of the EM spectrum, preferably symmetrically around the absorption peak, with a max/min band limit of +/−15% of the absorption peak value. In case of infrared radiation, a corresponding band is advantageously chosen to match an absorption peak of the chemical component of interest. In an embodiment, the photoacoustic gas sensor device is used as a $CO_2$ sensor. In that case the band of infrared radiation is centered around a wavelength of 4.3 μm. Preferably the band has a full width at half maximum of below 0.5 μm, which may be understood as a narrow band.

The EM radiation source may be a broadband radiation source which is defined as emitting radiation of a wide spectrum, such as across the entire infrared spectrum or e.g. between 0.8 μm and 10 μm. Such broadband source may be a conventional infrared emitter with a heater. The broadband source is preferably covered by a bandpass filter, e.g. a dielectric filter, or a meta-material filter, or a CMOS absorption layer, such that only infrared radiation of the band is emitted into the measurement volume. In another embodiment, a narrow band EM radiation source is used, such as a laser, or an LED, possibly comprising a meta-surface resonator.

The pressure transducer resides in the measurement volume and/or is acoustically coupled with the measurement volume in order to detect pressure variations occurring therein in response to the PA coupling in the presence of the chemical components desired to be detected. In embodiments, the pressure transducer may either be a general pressure transducer, or a microphone, in particular sensitive to only a certain range of frequencies around the modulation frequency. The pressure transducer can a bottom port microphone, with the bottom port facing the substrate.

In an embodiment, the substrate is a printed circuit board (PCB), e.g. made from FR4, or a ceramic material which provides more mechanical stability. At least the pressure transducer, the electromagnetic radiation source, the controller, as well as the measurement cell body and the cap are mounted on a common side of the substrate, i.e. the first side. Preferably all electronic components are mounted on the first side of the substrate. Preferably all electronic components are surface mounted on the first side of the substrate such that the photoacoustic gas sensor device is a SMD (surface mounted device). Preferably, a second side of the substrate, i.e. opposite the first side, only includes contacts for electrically connecting the photoacoustic gas sensor device to a carrier. In an embodiment, the contacts include land grid array (LGA) pads arranged for SMD assembly and/or reflow soldering. This facilitates an assembly of the device with other components by the customer. Other choices of contacts may include DFN, QFN or castellated holes.

In one embodiment, the cap may be of planar shape. Then, the cap volume is substantially defined by a recess in the substrate, i.e. a recess extending from the first side of the substrate. Accordingly, the substrate is thinned in its recessed portion compared to its regular thickness. Such recessed portion of the substrate then is covered by the planar cap. In this embodiment, it is preferred that the substrate is embodied as printed circuit board (PCB), or as a ceramic circuit board, comprising conducting paths. The PCB preferably is a multilayer PCB comprising multiple structured metallized layers conducting paths are made from at different levels of the PCB. Such PCB can be etched or ground or otherwise treated, preferably from its first/front side, thereby removing material and generating the recess in the substrate. Such treatment may also include pre-structuring of individual layers of the PCB, e.g. by cutting of shaping, prior to laminating such layers to each other. However, the substrate is not treated so as to generate a through hole in the recessed portion. Instead, the substrate remains thinned in its recessed portion. In other words, the substrate is a continuous substrate even in the region of the recess.

In this embodiment, the at least one electrical component other than the pressure transducer is arranged in the recessed portion of the substrate. The planar cap closes the recess in the substrate and builds/defines an acoustically tight compartment and hence a cap volume together with the recessed portion of the substrate.

In particular, the planar cap is made from metal, given that its surface faces the measurement cell and is desired to be of reflective property. In another embodiment, the cap, and preferably at least the side of the cap facing the measurement volume, is coated by a reflective coating, such as gold.

Preferably, at least the controller is arranged on the substrate in its recessed portion. In case only the controller and/or any component not requiring access to the measurement volume is/are arranged in the cap volume, the planar cap may be a continuous sheet of the desired, potentially opaque material and fully cover and/or seal the recess in the substrate. However, in case the electromagnetic radiation source is arranged in the recessed portion of the substrate the cap preferably comprises an opening covered by a transparent material in case the cap is not transparent for the electromagnetic radiation emitted by the electromagnetic radiation source. Such opening preferably is covered by an optical filter transparent for the electromagnetic radiation in order to enable the electromagnetic radiation generated in the cap volume to transit through the optical filter into the measurement volume. The optical filter preferably is sealed to the cap.

In a different embodiment, the cap is made from silicon. Again, in case only the controller and/or any component not requiring access to the measurement volume is/are arranged in the cap volume, the planar cap may be a continuous sheet of the desired material and fully cover and/or seal the recess in the substrate, and even may be opaque or coated by an opaque material. However, in case the electromagnetic radiation source is arranged in the recessed portion of the substrate, the silicon cap either is permeable for the electromagnetic radiation generated in the cap volume, or comprises an opening, or comprises a transparent section. Preferably, an optical filter transparent for the electromagnetic radiation, and preferably only for the electromagnetic radiation of a certain wavelength, is applied to the cap, either as element separate from the silicon cap, or as optical coating deposited—e.g. by PECVD—on the silicon cap in form of a layer, to one or both sides of the cap, i.e. either facing the measurement cell or facing the substrate, or facing both. In a different embodiment, the optical filter is integrated into the cap and hence may represent a portion of the cap. Such portion may either be of different optical property than other portions of the cap. In an alternative, the entire cap may be manufactured from a material with the desired optical property, however, only a portion of is prepared to let the electromagnetic radiation pass given that the other portions of the cap may be optically impaired e.g. by way of an optically opaque coating on such portions.

The recess effects a thinned substrate with an upper surface representing the first side of the substrate. The upper surface, also referred to as first level surface, resides on a first level of a vertical axis in case the substrate has a thickness along the vertical axis and a planar extension along the x- and y-axis. The first level surface is lower than the regular surface level of the substrate. The first level surface may be a planar surface to place one or more of the electrical components on. This may imply, in one embodiment, that the first level surface exposes contact pads to electrically contact the one or more electrical components. Such contact pads may be formed from one of the metallized layers in the PCB, such that the first level surface may be on a level exceeding the level of this metallization layer in the PCB somewhat. Accordingly, the PCB may be ground or etched or otherwise treated down to such first level to generate the recess that enables electrical components to be easily electrically contacted.

In another embodiment, the recess is shaped such that surfaces on two different levels along the vertical axis are generated, wherein the second level surface is lower than the first level surface. In particular, the second level surface is arranged between first level surfaces, such that the first side of the substrate shows the following profile: regular level, step down to the first level, step down to the second level, step up to the first level, step up to the regular level. Accordingly, a component that requires a backside volume may be arranged on the first level surface bridging the second level surface. Such electrical component preferably is the electromagnetic radiation source. In a different scenario, components may be arranged on the second level surface which components show a thickness that prohibits their arrangement on the first level surface in view of the cap.

In the embodiment with a recessed portion of the substrate, further components to be arranged outside the cap volume may in one embodiment be placed on non-recessed portions of the substrate, i.e. on its regular level. However, in a different embodiment, another recess may be provided in the substrate, at its first side, generating a third level surface for placing or SMD mounting such components on. Such other recess preferably is covered by a cover. The other recessed portion of the substrate and the cover form another cap volume. This other cap volume is not connected with the cap volume. In case the cover is reflective and/or the cover is coated by a reflective coating, at least on the side facing the measurement volume, the reflectivity in the measurement volume is enhanced and facilitated compared to providing components with reflective surfaces. The level of the third surface in the other recessed portion may be identical to the level of the first surface in the recessed portion, but not necessarily needs to. Preferably, the pressure transducer is arranged on the substrate in its other recessed portion. However, further components may be arranged in the other recessed portion of the substrate.

Most preferably, the cover for the other recess is represented by the cap for the recess. Accordingly, the cap may be elongate and also cover the other recess. For the material of such cover, it is referred to the material of the cap. Preferably, also the cover is coated by a reflective coating in one instance, which reflective coating faces the measurement volume. Preferably, the coating may be a continuous coating on the cap and the cover.

In case the pressure transducer is arranged in the other recessed portion, it is preferred that the cover comprises an opening for acoustically coupling the measurement volume with the volume underneath the cover, which volume is also referred to as other cap volume. The opening is dimensioned such that the acoustic coupling between the measurement volume and the other cap volume allows acoustic waves generated in the measurement volume be detected by the pressure transducer.

In another embodiment, the other recess is shaped such that surfaces are generated on two different levels along the vertical axis, wherein a fourth level surface is lower than the third level surface. In particular, the fourth level surface is arranged between third level surfaces, such that the first side of the substrate shows a profile in the other recessed portion as follows: regular level, step down to the third level, step down to the fourth level, step up to the third level, step up to the regular level. A component that requires a backside volume preferably is arranged on the third level surface bringing the fourth level surface. Such electrical component preferably is the pressure transducer. In a different scenario, one or more components may be arranged on the fourth level surface which components show a thickness that prohibits their arrangement on the third level surface in view of the cap. Preferably, the third level is equal to the first level. Preferably, the fourth level is equal to the second level.

In a different embodiment of the cap, a cap structure is provided containing a first cavity for forming the cap and another cavity for forming another cap. The first cavity partially or completely contributes to the cap volume. The second cavity partially or completely contributes to another cap volume, in combination with the substrate. The cap volume and the other cap volume are separated from each other by means of the cap structure e.g. by means of a base of the cap structure to sit on the substrate. While one or more electrical components other than the pressure transducer are placed in the cap volume, the pressure transducer now is placed in the other cap volume. The cap structure preferably shows an opening towards the measurement volume for acoustically coupling the measurement volume to the pressure transducer.

In such embodiment, the electrical components may all reside on the first side of the substrate. However, in comparison with other embodiments with a single cap, other electronic components to be arranged outside the cap, such as the pressure transducer, are also capped by means of the other cap. Preferably both caps are manufactured from a common cap structure which may be embodied as a silicon wafer or as a printed circuit board (PCB) with two cavities forming the two caps. In case of a silicon wafer, known processes such as etching can be applied for generating the cavities. In case of a PCB, processes such as disclosed for generating the one or more recesses in the PCB substrate can be applied for generating the cavities. As a result, even the other electrical components do not directly face the measurement volume but are arranged in the other cap volume that is coupled with the measurement volume by means of the one or more openings in the cap structure. Again, it is preferred that at least the surface of the cap structure facing the measurement volume is reflective or coated by a reflective coating.

The substrate nevertheless may also comprise a recess to offer a first level surface at a lower level than the regular level surface of the substrate. Such recess may be used as back volume e.g. for the electromagnetic radiation source.

The portion of the substrate capped by the other cap may also comprise another recess to offer a third level surface at a lower level than the regular level surface of the substrate. Such other recess may be used as back volume e.g. for the pressure transducer.

Preferably, the cap structure is attached to the substrate with the cavities facing the substrate, by one of bonding, in particular if case the cap structure is a silicon wafer, or by gluing or soldering, in case the cap structure is made from a PCB. In case the cap structure has the same or a similar footprint (+/−10%) in x-/y-direction as the substrate, the measurement cell body preferably is attached to the cap structure. Hence, the cap structure acts as intermediate element between the substrate and the measurement cell body. In another embodiment, the cap structure may have a smaller footprint than the substrate. Still, the measurement cell body can be attached to the cap structure while the substrate shows a portion neither covered by the measurement cell body nor by the cap structure for implementing circuitry on.

Preferably, the aperture in the measurement cell allows a gas exchange between the measurement volume and surroundings of the measurement cell. The aperture may be provided in the measurement cell body or in the substrate. In an embodiment, a gas permeable membrane covers the aperture. The membrane is permeable for a gas exchange between the measurement volume and surroundings of the measurement cell. The gas permeable membrane may in particular be made of one or more of the following materials: sintered metal, ceramic, polymer. The membrane advantageously also acts as a decoupling element between the measurement volume and the surroundings of the measurement cell. Thus it preferably damps a movement of gas molecules through the membrane such that pressure variations, e.g. sound waves, from the surroundings are damped when propagating into the measurement volume, and pressure variations inside the measurement volume are largely kept inside.

In case of the presence of the other recess in the substrate and/or the cap structure forming two caps such as laid out above, i.e. in case of the other cap volume implemented next to the cap volume, the aperture preferably is implemented as a though-hole in the substrate terminating in the other cap volume. In one embodiment thereof, the opening in the cover or cap structure provided for the acoustic coupling of the pressure transducer may also be sufficient for the desired gas exchange between the ambient and the measurement volume, via the other cap volume. In a different embodiment, a further opening may be provided in the cover or cap structure serving the gas exchange between the ambient and the measurement volume, which further opening is arranged closer to the aperture in the substrate than the first opening that is arranged closer to the pressure transducer. Accordingly, the (first) opening in the cover or cap structure may primarily be dedicated to the acoustic coupling in view of its location closer to the pressure transducer than to the through-hole in the substrate. The other (second) opening in the cover or cap structure may primarily be dedicated to the gas exchange in view of its location closer to the aperture in the substrate than to the pressure transducer.

In any case, a membrane may be provided covering the aperture, the membrane preferably being arranged on the first side of the substrate.

In such scenarios, another sensor as laid out above may also be arranged in the other cap volume in view of the aperture terminating in the other cap volume. Hence, such other sensor may sense one or more parameters of the ambient in view of its access to the ambient via the aperture.

In a further embodiment, however, in combination with the other recess in the substrate and/or the cover or the cap structure implementing the second cap volume, a further cap volume may be provided that is separated from the other cap volumes. The aperture terminates in the further cap volume. Accordingly, a gas exchange between the ambient and the measurement volume is effected by the further cap volume, thereby not affecting the measurement by the pressure transducer in the other cap volume. And/or the path for the gas to exchange between the ambient and the measurement volume may be shorter than via the other cap volume.

In case of the planar cap/cover, the further cap volume is preferably built by a further recess in the substrate separated from the other recesses by a portion of the substrate reaching its regular level of thickness. The cover for the further recess may specifically be represented by the elongated cap at the same time representing the cover for the other recess. In case of the cap structure, the further cap volume is preferably built by a further cavity in the cap structure separated from the other cavities by a base to sit on the substrate after mounting.

In such embodiment, the cover/cap/cap structure comprises a further opening in order to connect the further cap volume with the measurement volume 21 and allow for a gas exchange with the ambient. In such embodiment, a membrane may be arranged on the aperture in the substrate, but may alternatively be arranged on the cap/cover/cap structure covering the further opening, or being integrated into the cover/cap/cap structure e.g. by etching.

Summarizing, in case of the substrate providing for the aperture for the gas exchange between the ambient and the measurement volume, three scenarios are preferred: 1) The aperture directly terminates in the measurement volume. 2) The aperture terminates in the other cap volume, such that the gas reaches the measurement volume via the other cap volume through an opening in the cover or cap structure. 3) The aperture terminates in a further cap volume, such that the gas reaches the measurement volume from the ambient via the further cap volume, through an opening in the cover or cap structure.

The PA gas sensor device can be used in many different fields of applications due to its small dimensions/footprint: These may include, but not limited to table top or portable devices for measuring quality of air, wall mounted thermostats, probes in air ducts, etc.

According to a further aspect of the present invention, a method is provided for manufacturing a photoacoustic gas sensor device for determining a value indicative of a presence or a concentration of a chemical component in a gas. A substrate is provided, preferably comprising conductor tracks for electrically interconnecting electrical components. The electrical components are mounted on a first side of the substrate, preferably in a SMD process. The electrical components comprise at least an electromagnetic radiation source for emitting electromagnetic radiation, a pressure transducer for measuring a sound wave generated by the chemical component in response to an absorption of electromagnetic radiation by the chemical component, and a controller configured to control the electromagnetic radiation source. A cap is mounted on the first side of the substrate. The cap and the substrate acoustically seal a cap volume. The cap encloses at least one of the electrical components other than the pressure transducer.

A measurement cell body is mounted on the first side of the substrate thereby enclosing the cap and electrical components arranged outside the cap, and thereby, together with the substrate, defining a measurement cell. The measurement cell body and the substrate form a measurement cell. The measurement cell body, the substrate and the cap confine a measurement volume into which the electromagnetic radiation is emitted. The measurement cell comprises an aperture for the gas to enter the measurement volume.

In one embodiment, prior to mounting the electrical components on the first side of the substrate, a recess is generated in the substrate at its first side, e.g. by one of the processes disclosed above. The electrical components are then mounted on the first side of the substrate in its recessed portion and outside the recessed portion prior to applying the cap.

During ongoing assembly of the PA gas sensor device, the already mounted cap may in addition mechanically protect any electrical component/s underneath, in particular from mechanical impact, from dust and/or liquids, from adhesives and/or solder used for subsequently mounting components to the substrate.

Preferably, the mounting of the cap to the substrate includes one of gluing or soldering. In particular soldering is preferred, most preferably with a solder alloy with a melting point above those of commonly used soldering alloys for resisting high temperatures, in order to allow a customer soldering the PA gas sensor device into the designated system PCB, for example. In such scenario, it is proposed to use a glue/an adhesive with a melting point exceeding the melting point of solder, and in particular of the solder expected to be used for soldering the PA gas sensor device onto a system PCB. Then, a customer can be free in using any attachment technique without risking the cap resolving from the substrate. The same may be true for mounting the measurement cell body, i.e. adhering the measurement cell body to the substrate by means of an adhesive, and preferably an adhesive with the above melting characteristics is preferred. In case of adhering both the cap and the measurement cell body to the substrate, both adhesives may be annealed in the same step, i.e. concurrently.

Other advantageous embodiments of photodetector are listed in the dependent claims as well as in the description below.

BRIEF DESCRIPTION OF THE DRAWINGS

Embodiments of the present invention, aspects and advantages will become apparent from the following detailed description thereof. The detailed description makes reference to the annexed drawings, wherein the figures show.

DETAILED DESCRIPTION OF THE DRAWINGS

Figure 1:
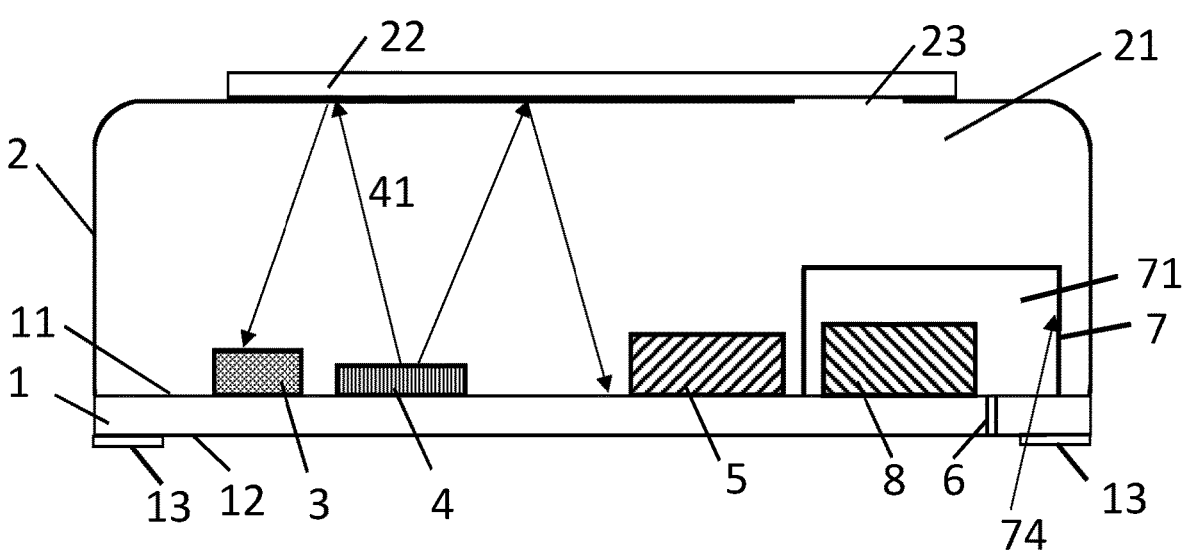
FIG. 1 a cut view of a photoacoustic gas sensor device according to an embodiment of the invention, FIG. 2 a cut top view of a photoacoustic gas sensor device according to an embodiment of the invention, FIGS. 3 to 8, each a cut view of a photoacoustic gas sensor device according to an embodiment of the invention.

Same elements are referred to by same reference numerals across all figures.

FIG. 1 shows a cut view of a photoacoustic (PA) gas sensor device according to an embodiment of the present invention. The PA gas sensor device comprises a substrate 1, e.g. a printed circuit board (PCB), and a measurement cell body 2, which together form a measurement cell enclosing a measurement volume 21. The measurement cell has an aperture 23 to allow an exchange of gas between the measurement volume 21 and the ambient of the PA gas sensor device. In FIG. 1, the aperture 23 is located in the measurement cell body 2. The aperture 23 is preferably covered by a membrane 22 which is gas permeable to allow for a gas exchange such that a concentration of the chemical component of interest in the gas is similar as in the ambient.

The substrate 1 has a first side 11 and a second side 12. The measurement cell body 2 is arranged on the first side 11, as well as electrical components described below. On the second side 12 of the substrate opposite the first side 11, pads 13 are provided, e.g. land grid array (LGA) pads, for SMD assembly and reflow soldering by a customer. Other contacts such as DFN, QFN pads or castellated holes are possible.

The electrical components arranged on the first side 11 of the substrate 1 comprise a pressure transducer 3 and an electromagnetic radiation source 4, which in this example is an infrared source. Both electrical components are located inside the measurement volume 21.

The infrared source emits infrared radiation indicated by reference sign 41. The infrared radiation 41 is selectively absorbed by molecules of a chemical component of interest resident in the measurement volume 21 in case the wavelength/band of the radiation emitted by the infrared source is adjusted to the gas molecules to be detected. The infrared source may be a broadband infrared emitter, e.g. emitting radiation over the entire infrared spectrum, covered with an optical bandpass filter. The optical bandpass filter only lets pass radiation of a band that is set according to the gas component of interest. For a detection of $CO_2$, the band is for instance centered around 4.3 μm, and has a typical band width of 0.5 μm, or smaller, e.g. 0.2 μm or 0.1 μm, such that a measured value is actually selective on $CO_2$.

The pressure transducer 3 may be a MEMS microphone or any other pressure transducer. A sensitivity of the pressure transducer is not necessarily limited to an acoustic frequency band but may be configured to measure frequencies up to 100 kHz. One or more other electrical components may be arranged on the first side 11 of the substrate 1 and are collectively referred to by 5.

In addition, a cap 7 with a cavity 74 is arranged on the first side 11 of the substrate 1 within the measurement cell. The cap 7 delimits the measurement volume 21 from a capped volume 71 which is defined by the substrate 1 and the cap 7. A controller 8 is arranged in the cap volume 71, i.e. the controller 8 is enclosed by the cap 7. The pressure transducer 3, the electromagnetic radiation source 4, the controller 8 and the other components 5 if any are electrically connected via electrical conductor tracks in or on the substrate 1.

In a very preferred embodiment, the controller 8 is embodied as an ASIC. The controller 8 in one embodiment may receive and process signals from the pressure transducer 3 and one or more other sensors if available. The controller 8 controls the EM radiation source 4, and may provide a PA gas sensor device signal e.g. represented by a processed or at least preprocessed signal from the pressure transducer 3 to the outside. For these reasons, the substrate 1 preferably comprises through vias (not shown) for connecting the conductor tracks e.g. provided on the first side 11 of the substrate 1 to the aforementioned pads 13 on the second side 12 of the substrate 1. Preferably, the substrate 1 comprises multiple layers of conductive tracks, such as an FR4-PCB.

Accordingly, the controller 8 is configured to control the EM radiation source 4, e.g. by imposing an intensity modulation on the infrared radiation with a modulation frequency. The modulation frequency may be within the audible spectrum, e.g. between 20 Hz and 20 kHz, or it may be up to 100 kHz, or it may even be down to 5 Hz. The controller 8 is further configured for receiving measurement values from the pressure transducer 3, as well as for determining a value of the chemical component concentration from those measurement values, e.g. by using a predefined or a resettable calibration function linking the measurement values to concentrations value of the chemical component. The value of the chemical component concentration may be output via a digital interface, e.g. an I2C interface. When determining the value of the chemical component concentration, the controller 8 may also take into account measurement values of one or more other, if available, e.g. temperature and/or humidity values, and perform a compensation as described above. For $CO_2$ as the relevant gas component, measurements in the range between 0 and 10'000 ppm, or between 0 and 40'000 ppm, or between 0 and 60'000 ppm $CO_2$ are possible.

The substrate 1 preferably comprises a through-channel within its capped area from its first side 11 to its second side 12, which through-channel serves as a venting hole 6 for allowing e.g. over- or under pressure to align with the pressure of the ambient, and/or for allowing gas in the cap volume 71 to escape and/or for allowing gas of the ambient to enter the cap volume 71.

Figure 2:
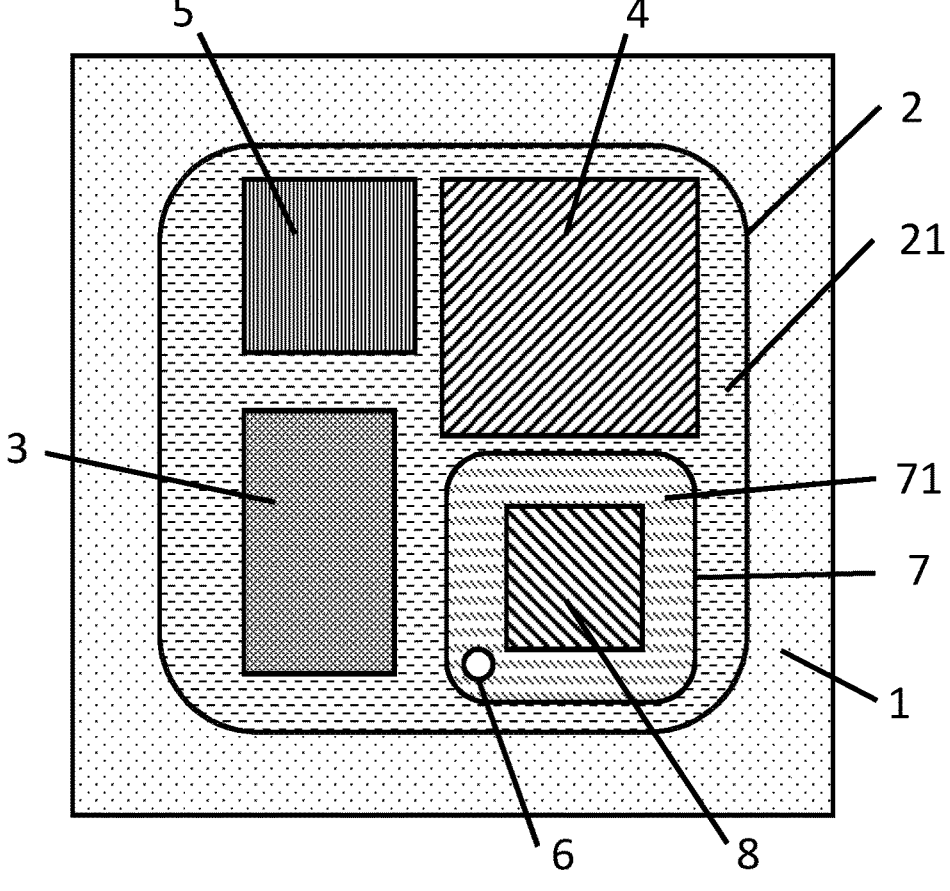

FIG. 2 shows a cut top view of a PA gas sensor device according to an embodiment of the invention. In this embodiment, the substrate 1 has a square base area, onto which the measurement cell body 2 is mounted. Within the measurement cell body 2 the electrical components are arranged, e.g. in four quadrant-like sections. The pressure transducer 3 and the EM radiation source 4 are arranged in opposite quadrants. The other components 5 and the controller 8 are arranged in the remaining two opposite quadrants. The controller 8 is capped by a cap 7. The resulting cap volume 71 is linked to the surroundings of the PA sensor device by means of a venting hole 6.

FIG. 3 shows a cut view of a PA gas sensor device according to an embodiment of the invention. In this embodiment, an EM radiation source 4, a pressure transducer 3 and a capacitor 51 are arranged on the first side 11 of a substrate 1 facing the measurement volume 21 defined by the substrate 1 and a measurement cell body 1 arranged on the same first side 11 of the substrate 1. A controller 8 embodied as ASIC is arranged on the very same first side 11 of the substrate 1, however is capped by cap 7. A venting hole 6 is provided through the substrate 1 for balancing pressure in the cap volume 71. On the second side 12 of the substrate 1, the venting hole 6 is covered by a venting hole membrane 14 allowing gas from or into the cap volume 71 to pass.

In addition, another sensor 9 is provided which advantageously is one or more of the following: a temperature sensor, a humidity sensor, a combined temperature/humidity sensor, a pressure sensor, in particular a barometric pressure sensor, another pressure transducer, another gas sensor, e.g. of metal oxide type or of electrochemical type. Through measurement values of temperature and/or humidity, a gas concentration value may be compensated, e.g. for effects of temperature and/or humidity. In the presence of the other sensor 9, the controller 8 in the cap volume 71 preferably is configured to compensate the value indicative of a presence or a concentration of the chemical component for the impact of the variable measured by the other sensor 9 and hence, dependent on measurement values of the other sensor 9. Hence effects of ambient conditions on the measurement of the chemical component can be reduced or eliminated.

FIG. 4 shows a cut view of a PA gas sensor device according to a further embodiment of the present invention.

In comparison with the embodiment shown in FIG. 3 not only the controller 8 is capped within the measurement cell, but also one or more other electrical components such as the capacitor 51 illustrated, as is the electromagnetic radiation source 4. The latter requires an optical window 72 in the cap 7. The optical window 72 enables the radiation emitted by the EM radiation source 4 to enter the measurement volume 21 and interact with the gas molecules of interest. In this embodiment, the pressure transducer 3 remains arranged in the measurement volume 21 outside the cap volume 71. The pressure transducer 3 thus is enabled to detect the pressure variations induced by the reaction of the gas molecules with the emitted radiation.

In this embodiment, again another sensor 9 is provided. In this example, the other sensor 9 is a humidity sensor. The humidity sensor may provide its signal representing the humidity measured inside the measurement cell to the controller 8 which may be used to compensate the pressure transducer signal for humidity induced variations. Presently, the cap volume 71 is not connected to the outside world given that there is no venting hole. However, in a different embodiment, a venting hole may indeed be provided for the above reasons.

FIG. 5 shows a cut view of a PA gas sensor device according to a further embodiment of the present invention. In comparison with the embodiment shown in FIG. 4 the other sensor 9—again a humidity sensor—is now arranged under the cap 7, i.e. within the cap volume 71. Accordingly, the signal provided by the pressure transducer 3 again may be compensated by humidity variations. In the present example, a venting hole 6 and a venting hole membrane 14 are provided for allowing venting the cap volume 71. In this embodiment, the pressure transducer 3 is one of or even the only component not arranged in the capped volume 71. Such approach improves, i.e. increases a mean optical path length of the radiation 41 within the measurement volume 21. This is achieved by one or more of the following options: A material of the measurement cell body 2 is chosen to be reflective, such as a sheet metal. Alternatively, or additionally, an inner surface of the measurement cell body 2 is coated with a reflective coating. The reflective coating may not only be arranged on an inner surface of the measurement cell body 2, but also on one or more of the following: parts of the first side 11 of the substrate 1; on parts of the pressure transducer 3, such as its top side; on the outer surface of the cap 7 facing the measurement volume 21. In this way, the overall reflectivity inside the measurement cell is increased, which leads to more accurate measurements of the concentration of the component.

Figures 6, 7:
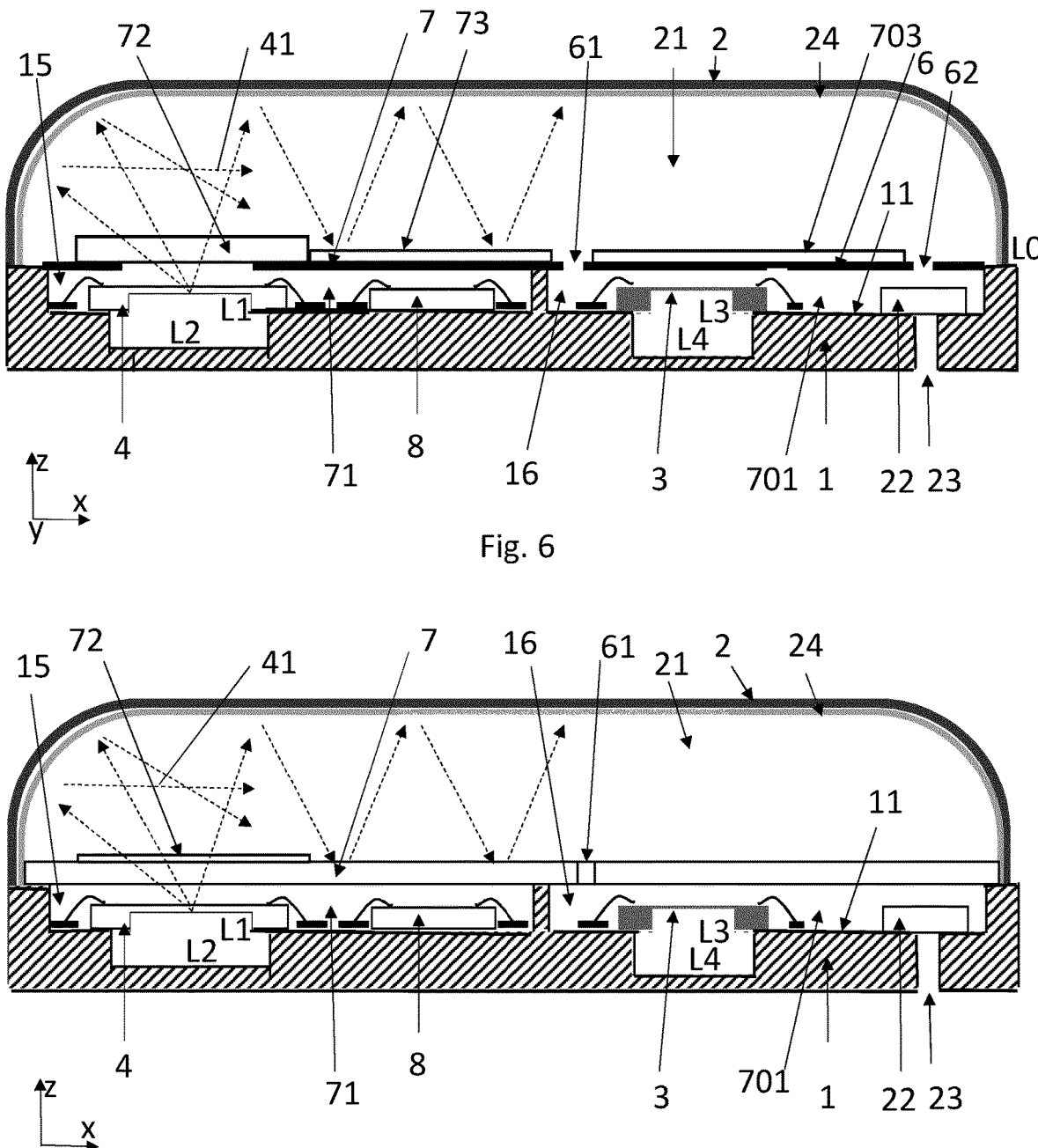

FIG. 6 and FIG. 7 each shows a cut view of a photoacoustic (PA) gas sensor device according to further embodiments of the present invention. In the previous embodiments, the cap itself contributed significantly to the cap volume in that the cap itself provided a cavity and hence defined an interior space. In the embodiments of FIGS. 6 and 7, the cap is embodied as planar cover while the cap volume is defined by a recess in the substrate.

In the embodiments of FIGS. 6 and 7, the substrate 1 preferably is a printed circuit board (PCB), preferably a multilayer PCB comprising multiple conducting layers at different vertical levels of the PCB. The PCB is structured e.g. by etching or grounding or other material removing techniques in order to generate at least one recess 15 in the PCB resulting in a recessed portion of the PCB. The recess 15 is located on the first side 11 of the PCB, i.e. the side 11 on which the components are/will be arranged at. The recess 15 is understood as an indentation, not as a through channel, such that in the recessed portion of the substrate 1 the substrate 1 is thinned compared to its regular thickness. In other words, the substrate 1 is a continuous substrate 1 also across its recessed portion.

The recess 15 in the substrate 1 effects a first level L1 surface, and a second level L2 surface lower than the first level L1 along the z-axis. On this first level L1 surface, presently two components are arranged, i.e. the electromagnetic radiation source 4 and the controller 8. As can be seen in FIGS. 6 and 7, these components 4, 8 are bond wired to the first level L1 surface of the substrate 1, hence implying that the first level L1 represents a level of the substrate 1, in which one of the conductive layers is structured to produce conductive paths and contact pads. The electromagnetic radiation source 4 bridges the second level L2 surface.

The substrate 1 comprises a second recess 16. The pressure transducer 3 is arranged in the second recess 16 on a third level L3 surface, bridging a fourth level L4 surface of the second recess 16. The pressure transducer 3 is electrically connected to conducting pads/paths of a metallization layer in the substrate 1. The aperture 23 presently is provided in the substrate 1, covered by a membrane 22 on the first side 11 of the substrate 1 in its other recessed portion.

In the embodiment of FIG. 6, the recess 15 is closed by a planar cap 7. The other recess 16 is closed by a planar cover 6. The cap 7 supports a reflective coating 73 facing the measurement volume 21. The cover 6 supports a reflective coating 703 facing the measurement volume 21. Cap 7 and recessed portion of the substrate 1 define the cap volume 71. Cover 6 and the other recessed portion of the substrate 1 define another cap volume 701. Preferably, the cap 7 and the cover 6 are one piece, with a uniform coating 73,703.

The cover 6 provides for two openings 61 and 62. Opening 61 is arranged close to the pressure transducer 3 and provides for an acoustic coupling between the measurement volume 21 and the pressure transducer 3. Opening 62 is close/above the aperture 23 and specifically supports gas exchange between the ambient and the measurement volume 21.

In the embodiment of FIG. 7, the recess 15 and the other recess 16 are closed by a planar cap 7 of one piece made from silicon. The other recess 16 is closed by the planar cap 7. The cap 7 itself is of reflective material. The cap 7 provides for an opening 61 for both, acoustic coupling and gas exchange with the measurement volume 21. Cap 7 and recessed portion of the substrate 1 define the cap volume 71, and cap 7 and the other recessed portion of the substrate 1 define the other cap volume 701. Alternative electrical connections between the components and the substrate may include, solder balls, soldering or conductive adhesive.

Figure 8:
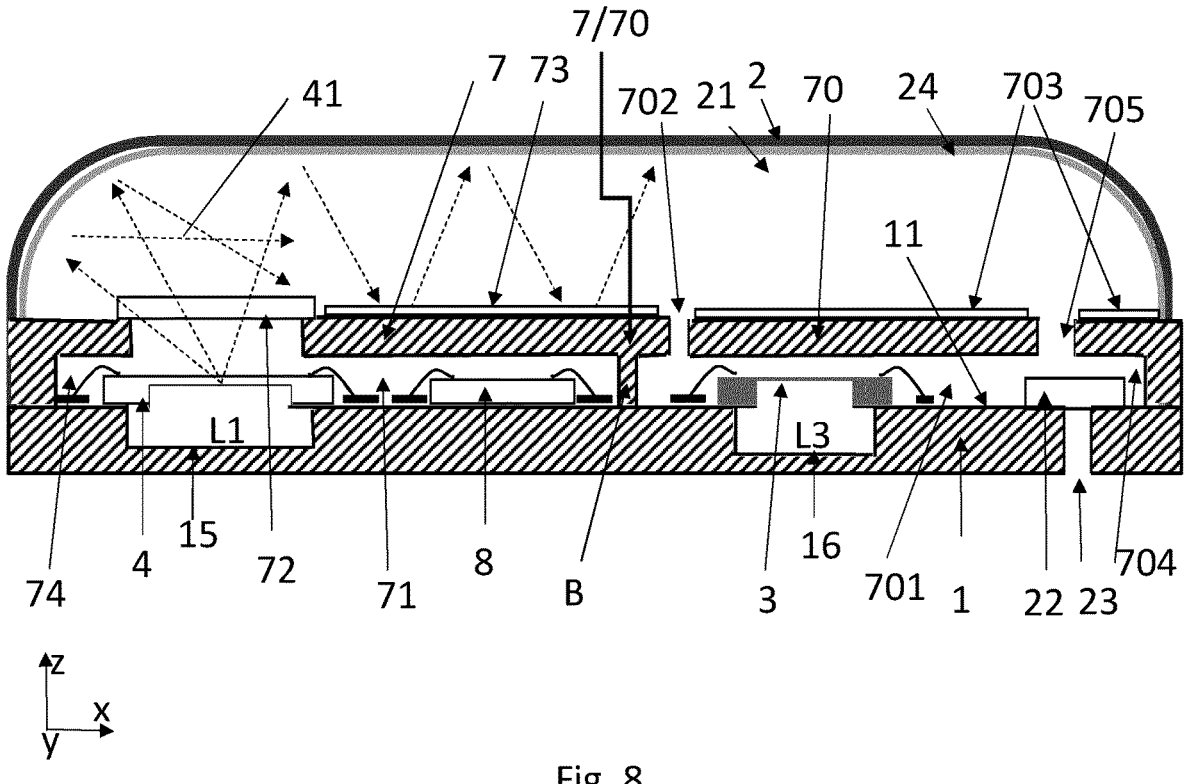

FIG. 8 illustrates a cut view of a photoacoustic gas sensor device according to another embodiment of the invention. The set up resembles the embodiments shown in FIGS. 6 and 7. However, the cap 7 no longer is a planar cover, but is formed by a cap structure 7/70 showing at least one cavity. Presently, the cap structure 7/70 includes a first cavity 74 for forming the cap 7 and another cavity 704 for forming another cap 70. Hence, the other cavity 704 is provided in order to contribute to another cap volume 701, in combination with the substrate 1 on which the cap structure 7/70 is arranged. The cap volume 71 and the other cap volume 701 are separated from each other by means of the cap structure 7/701 e.g. a base B in the cap structure 7/70 to sit on the substrate 1. While one or more electrical components other than the pressure transducer 3 are placed in the cap volume 71, the pressure transducer 3 is placed in the other cap volume 701. The cap structure 7/70 provides for at least one opening 702 for an acoustic coupling of the measurement volume 21 with the pressure transducer 3. This opening 702 is close to the location of the pressure transducer 3. A second opening 705 is provided for enabling a gas exchange between the ambient of the photoacoustic sensor and the measurement volume 21 via the other cap volume 701. For this purpose, the substrate 1 contains an aperture 23 close to the other opening 705, and a membrane 22.

In such embodiment, the electrical components may all reside on the first side 11 of the substrate 1 which substrate 1 may even show no recess or different surface levels. However, in comparison with other embodiments containing a single cap for capping few selected components, all components are presently capped. As a result, the components such as the pressure transducer 3 do not directly face the measurement volume 21, but the cap structure 7/70 instead. Given that any surfaces facing the measurement volume 21 are desired to be reflective, the cap structure 7/70 and at least its surface facing the measurement volume 21 is preferably made from a reflective material or is coated with a reflective material, such as coating 703. Such coating 703 can more easily be achieved than the coating or the housing of individual electrical components.

Preferably, the cap 7 and the other cap 70 are formed by a common cap structure 7/70 such as shown in FIG. 8. The common cap structure 7/70 may be a silicon wafer with two cavities 74, 704 etched to form the two caps 7/70. Such silicon wafer preferably is bonded onto the first side 11 of the substrate 1. In the present example, the measurement cell body 2 is attached to the cap structure 7/70, while still arranged on the first side 11 of the substrate 1.

The substrate 1 may nevertheless also comprise one or more recesses, presently two recesses 15, 16 to offer first and third level L1/L3 surfaces, respectively, both at a lower level L1/L3 than the regular level surface of the substrate. Such recesses 15, 16 may be used as back volume e.g. for the electromagnetic radiation source 4 and the pressure transducer 3.

While above there are shown and described embodiments of the invention, it is to be understood that the invention is not limited thereto but may be otherwise variously embodied and practiced within the scope of the following claims.

LIST OF REFERENCES

1 Substrate
11 first side
12 second side
13 pad
14 venting hole membrane
15 recess
16 other recess
17 venting hole
L1 first level
L2 second level
2 measurement cell body
21 measurement volume
22 membrane
23 through channel
24 coating
3 pressure transducer
4 EM radiation source
41 infrared radiation
5 capacitor
6 cover
61 first opening
62 second opening 7 cap
71 cap volume
72 optical filter
73 coating
74 cavity
70 other cap
701 other cap volume
702 first opening
7/70 cap structure
8 controller
9 other sensor

The invention claimed is:

1. A photoacoustic gas sensor device for determining a value indicative of a presence or a concentration of a chemical component in a gas, the photoacoustic gas sensor device comprising:
  a substrate,
  a measurement cell body arranged on a first side of the substrate, the substrate and the measurement cell body defining a measurement cell,
  a cap arranged on the first side of the substrate within the measurement cell, the cap and the substrate defining a cap volume, and the cap and the substrate acoustically sealing the cap volume,
  a measurement volume confined by the measurement cell body, the substrate and the cap,
  an aperture in the measurement cell for the gas to enter the measurement volume,
  electrical components arranged on the first side of the substrate and in the measurement cell, comprising at least:
    an electromagnetic radiation source for emitting electromagnetic radiation into the measurement volume,
    a pressure transducer for measuring a sound wave generated by the chemical component in response to an absorption of the electromagnetic radiation by the chemical component present in the measurement volume,
    a controller configured to control the electromagnetic radiation source,
  wherein the pressure transducer is arranged outside the cap volume and at least one of the electrical components other than the pressure transducer is arranged in the cap volume,
  wherein the controller is arranged in the cap volume, and
  wherein the controller is configured to process an electrical signal supplied by the pressure transducer that is indicative of the presence or the concentration of the chemical component in the gas.

2. The photoacoustic gas sensor device according to claim 1,
  wherein a surface of the cap facing the measurement volume has a reflectivity of more than 70%, preferably more than 80%, more preferably more than 90%, and preferably wherein an inner surface of the measurement cell body has a reflectivity of more than 70%, preferably more than 80%, more preferably more than 90%.

3. The photoacoustic gas sensor device according to claim 1,
  wherein at least one transistor, preferably a transistor of a voltage controller is arranged in the cap volume.

4. The photoacoustic gas sensor device according to claim 1,
  wherein the substrate comprises a venting hole arranged to connect the cap volume to an ambient of the photoacoustic gas sensor device, wherein at least one other sensor for sensing an environmental parameter in the ambient gas of the photoacoustic gas sensor device supplied to the other sensor through the venting hole is arranged in the cap volume.

5. The photoacoustic gas sensor device according to claim 4,
  wherein the controller is configured to determine the value indicative of the presence or the concentration of the chemical component in the gas dependent on an electrical signal supplied by the pressure transducer and dependent on an electrical signal supplied by the other sensor.

6. The photoacoustic gas sensor device according to claim 1,
  wherein the electromagnetic radiation source is arranged in the cap volume,
  wherein the cap includes an optical filter arranged and configured to enable the radiation emitted by the electromagnetic radiation source to enter the measurement volume and/or bandpass filter the radiation emitted by the electromagnetic radiation source before entering the measurement volume.

7. The photoacoustic gas sensor device according to claim 1,
  wherein the electromagnetic radiation source is configured to emit ultraviolet radiation,
  wherein the electromagnetic radiation source is arranged outside the cap volume,
  wherein the cap is made from a material opaque to ultraviolet radiation to protect the controller in the cap volume therefrom.

8. The photoacoustic gas sensor device according to claim 1,
  wherein the cap comprises an electrically conducting material,
  preferably wherein the cap is made from metal or from plastics coated with metal,
  preferably wherein the measurement cell body is made from metal or from plastics coated with metal,
  preferably wherein the cap and the measurement cell body are made from the same material.

9. The photoacoustic gas sensor device according to claim 1,
  comprising a recess in the substrate at its first side,
  wherein the substrate is a printed circuit board or is made from a ceramic material, and comprises conductive paths,
  wherein the at least one electrical component other than the pressure transducer is arranged on the substrate in its recessed portion,
  wherein the cap is of planar shape and closes the recess in the substrate,
  wherein the cap volume is defined at least by the recessed portion of the substrate and the planar cap,
  wherein the cap is made from metal, and/or
  wherein the cap is at least partly coated by a reflective coating,
  preferably wherein the reflective coating is made from gold,
  preferably wherein the controller is arranged on the substrate in its recessed portion.

10. The photoacoustic gas sensor device according to claim 1,
  comprising a recess in the substrate at its first side,
  wherein the substrate is a printed circuit board or is made from a ceramic material, and comprises conductive paths, wherein the at least one electrical component other than the pressure transducer is arranged on the substrate in its recessed portion, wherein the cap is of planar shape and closes the recess in the substrate, wherein the cap volume is defined at least by the recessed portion of the substrate and the planar cap, wherein the cap is made from silicon, preferably wherein the controller is arranged on the substrate in its recessed portion.

11. The photoacoustic gas sensor device according to claim 1, comprising a recess in the substrate at its first side, wherein the substrate is a printed circuit board or is made from a ceramic material, and comprises conductive paths, wherein the at least one electrical component other than the pressure transducer is arranged on the substrate in its recessed portion, wherein the recess effects a first level surface in the substrate supporting one or more of the electrical components, and a second level surface lower than the first level surface, wherein the electromagnetic radiation source is arranged on the first level surface bridging the second level surface.

12. The photoacoustic gas sensor device according to claim 1, comprising a recess in the substrate at its first side, wherein the substrate is a printed circuit board or is made from a ceramic material, and comprises conductive paths, wherein the at least one electrical component other than the pressure transducer is arranged on the substrate in its recessed portion, and the photoacoustic gas sensor device further comprising another recess in the substrate at its first side, wherein the pressure transducer is arranged on the substrate in its other recessed portion.

13. The photoacoustic gas sensor device according to claim 12, comprising a cover covering the other recess in the substrate, comprising an opening in the cover for acoustically coupling another cap volume between the other recessed portion of the substrate and the cover to the measurement volume, wherein the other recess effects a third level surface in the substrate supporting one or more of the electrical components, and a fourth level surface lower than the third level surface, wherein the electromagnetic radiation source is arranged on the third level surface bridging the fourth level surface, preferably wherein the cover is represented by the planar cap.

14. The photoacoustic gas sensor device according to claim 1, comprising a cap structure including a first cavity forming the cap and including another cavity forming another cap, wherein the cap structure is arranged on the first side of the substrate, resulting in the cap volume and another cap volume between the cap structure and the substrate, wherein the pressure transducer is arranged in the other cap volume, wherein the other cap includes at least one opening for acoustically coupling the measurement volume to the other cap volume.

15. The photoacoustic gas sensor device according to claim 14, wherein the cap structure is made from a silicon wafer bonded to the substrate, or wherein the cap structure is made from a printed circuit board soldered or glued to the substrate.

16. The photoacoustic gas sensor device according to claim 14, wherein the measurement cell body is attached to the cap structure, preferably wherein the cap structure has the same footprint as the substrate.

17. The photoacoustic gas sensor device according to claim 14, wherein the aperture is arranged in the substrate, wherein the aperture connects the measurement volume with the ambient by one of:

directly;

via the other cap volume;

via a further cap volume between a further recessed portion of the substrate and a cover therefore, and/or between the substrate and the cap structure, wherein the cover or the cap structure respectively is permeable for the gas to enter the measurement volume.

18. A method for manufacturing a photoacoustic gas sensor device for determining a value indicative of a presence or a concentration of a chemical component in a gas, the method comprising:

providing a substrate, mounting electrical components on a first side of the substrate, preferably in a SMD process, the electrical components comprising at least:

an electromagnetic radiation source for emitting electromagnetic radiation, a pressure transducer for measuring a sound wave generated by the chemical component in response to an absorption of electromagnetic radiation by the chemical component, a controller configured to control the electromagnetic radiation source and configured to process an electrical signal supplied by the pressure transducer that is indicative of the presence or the concentration of the chemical component in the gas, mounting a cap on the first side of the substrate, the cap and the substrate acoustically sealing a cap volume, and the cap enclosing at least the controller but not the pressure transducer, mounting a measurement cell body on the first side of the substrate thereby enclosing the cap and electrical components arranged outside the cap, wherein the measurement cell body and the substrate from a measurement cell, wherein the measurement cell body, the substrate and the cap confine a measurement volume into which the electromagnetic radiation is emitted, and wherein the measurement cell comprises an aperture for the gas to enter the measurement volume.

19. The method according to claim 18, wherein prior to mounting the electrical components on the first side of the substrate a recess is generated in the substrate, wherein the at least one of the electrical components other than the pressure transducer is mounted on the first side of the substrate in its recessed portion, and wherein the pressure transducer is mounted on the first side of the substrate outside the recessed portion.

\* \* \* \* \*